United States Patent
Mack

(10) Patent No.: US 10,231,880 B2
(45) Date of Patent: Mar. 19, 2019

(54) PRESSURE REMOTION DISC

(71) Applicant: Barry Mack, Paradise, CA (US)

(72) Inventor: Barry Mack, Paradise, CA (US)

( * ) Notice: Subject to any disclaimer, the term of this patent is extended or adjusted under 35 U.S.C. 154(b) by 372 days.

(21) Appl. No.: 15/248,320

(22) Filed: Aug. 26, 2016

(65) Prior Publication Data

US 2017/0056251 A1 Mar. 2, 2017

Related U.S. Application Data

(60) Provisional application No. 62/213,110, filed on Sep. 2, 2015.

(51) Int. Cl.
*A61F 13/06* (2006.01)
*A61F 13/02* (2006.01)

(52) U.S. Cl.
CPC ........ *A61F 13/067* (2013.01); *A61F 13/0253* (2013.01); *A61F 13/063* (2013.01)

(58) Field of Classification Search
CPC .... A61F 13/063; A61F 5/0111; A61F 5/0127; A61F 5/0113; A61F 5/0585; A61F 5/0102; A61F 13/0203; A61F 13/02; A61F 15/008; A61F 2013/00846; A61G 13/12
See application file for complete search history.

(56) References Cited

U.S. PATENT DOCUMENTS

| | | | |
|---|---|---|---|
| 852,023 A | 4/1907 | Klokee | |
| 1,656,135 A | 5/1927 | Blanchfield | |
| 1,847,973 A | 6/1927 | Morton | |
| 2,098,312 A | 11/1935 | Scholl | |
| 2,918,056 A | 11/1957 | Levitt | |
| 3,334,626 A | 8/1967 | Schimmel | |
| 4,212,296 A | 7/1980 | Schaar | |
| 6,471,986 B1 | 10/2002 | Cline et al. | |
| 8,230,620 B2 | 7/2012 | Ebel | |

OTHER PUBLICATIONS

Dr. Jills Felt "U" Shaped Callus Pads Amazon.com product information, Aug. 26, 2016, published on Amazon.com.

*Primary Examiner* — Ophelia A Hawthorne

(57) ABSTRACT

After a human body has formed one of numerous calluses or sores due to various conditions of the human condition the present invention offers a means to aid in pain relief and/or an aid in therapy for sores and skin conditions normally considered to be caused by pressure. The present invention seeks to provide a device designed explicitly to transfer weight or pressure from an area on the body that causes the excrescence to develop. The simplest form is designed for use with a condition known as "Intractable Planter Keratosis" or "IPK". Whether the IPK callus is caused from locomotion, or other sores caused by continual or inordinate pressure, the present invention in its simplest form is a thin disc approximately but not limited to 1" in diameter and a thickness of approximately but not limited to 0.036" with a hollow protrusion of approximately but not limited to 0.036" that covers a sore completely but isolated the sore from any contact with the disc or the protrusion. The mechanical work that the present invention provides is the transferal of substantially all pressure away from the sore and to healthy flesh areas immediately around the sore.

13 Claims, 5 Drawing Sheets

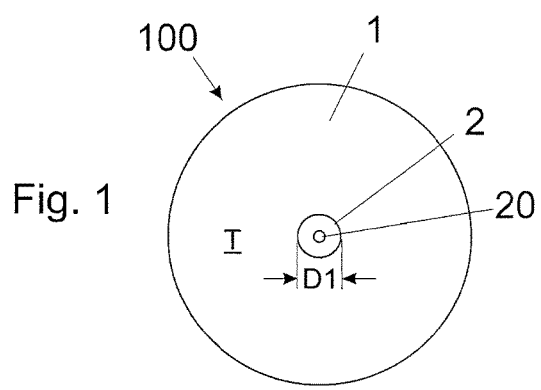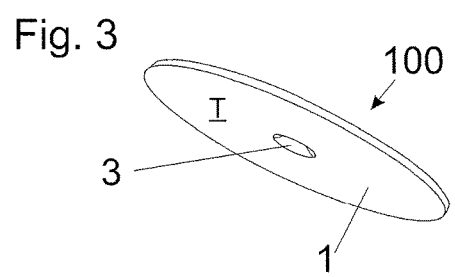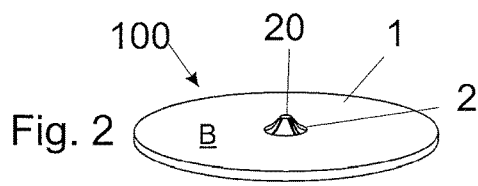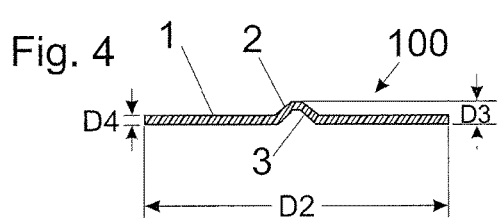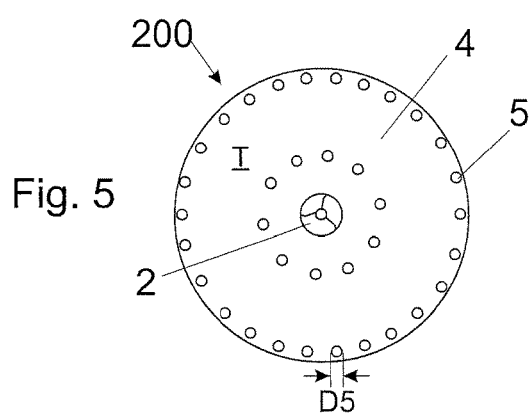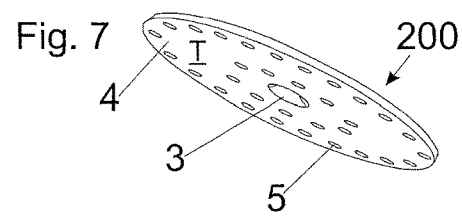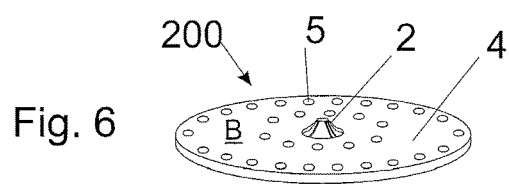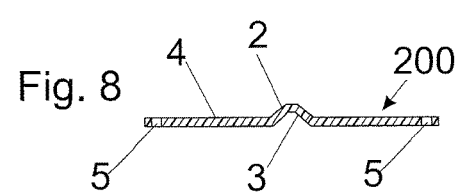

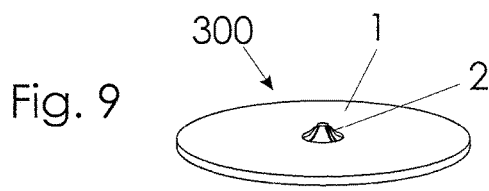
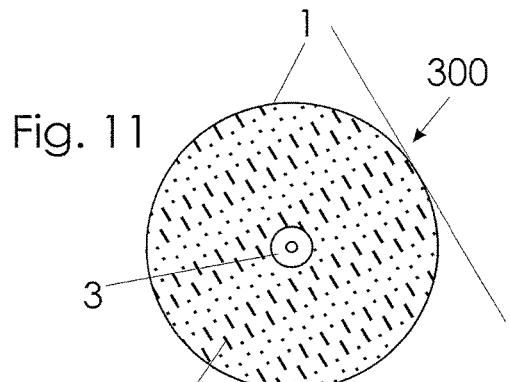
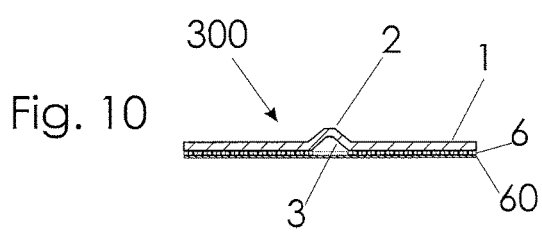
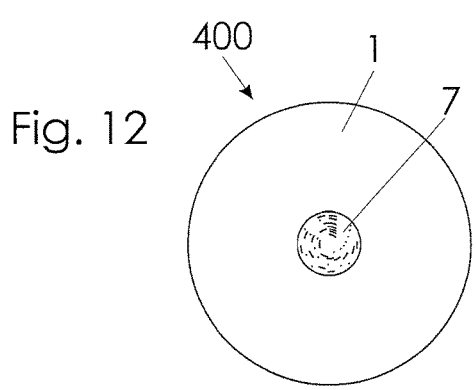
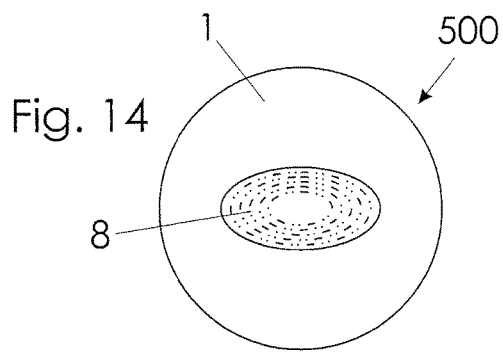
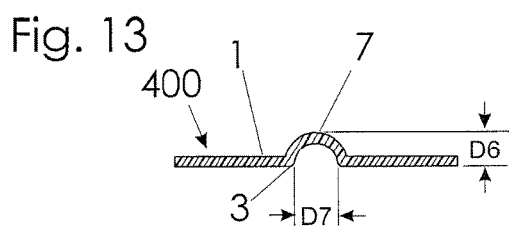
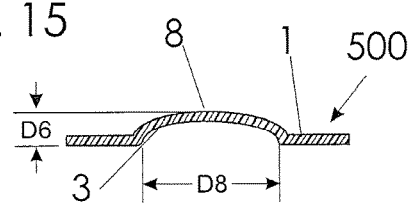

PRESSURE REMOTION DISC

CROSS REFERENCE APPLICATIONS

This application is a non-provisional application claiming the benefits of provisional application No. 62/213,110 filed Sep. 2, 2015.

FIELD OF INVENTION

The present invention relates to external treatment using a physical appliance under the foot to reduce pressure on an Intractable Planter Keratosis (IPK) and similar maladies.

BACKGROUND OF INVENTION

This invention falls typically into the category of foot care devices used to help alleviate pressure and friction from various types of sores that commonly develop on the foot. The new invention is a device more specifically designed for use with a condition known as Intractable Plantar Keratosis (IPK). This is a discrete focused callus located on the plantar aspect of the forefoot typically occurring beneath one or more lateral metatarsal heads or under another area of pressure. Other diagnosis of IPK may include Plantar Verrucous Carcinoma and Epidermal Inclusion Cyst. However, the present invention is not necessarily limited to (IPK) only, as it may be useful in aiding in pain relief or therapy of various types of sores found on the foot. The present invention and its inherent mechanical function could also be useful in conjunction with various pressure related sores on various parts of the human body. The present invention using the innate characteristics with applicable modifications to shape, width, depth, and thickness of the features can be used in isolating and promoting pain relief and therapeutical benefits including but not limited to warts, corns, calluses, bedsores, blisters, burns, lacerations etc. common to the human body. A method of creating a custom form fitting appliance is also included for adaptation for all of the human body's unique architectural shapes, areas and contours. It also should be noted that the present invention could also be used in the same manner with or without modifications in the treatment of animal sores in the veterinary field.

DESCRIPTION OF RELATED ART

There are many known types of foot care products. A walk into any typical drugstore will reveal an isle with many and various cushions, U pad cushions, mole skin, corn pads, corn cushions, liquid filled ampule cushions etc. Except for the "U" Pads these devices all have one thing in common; they contact the callus or blister or corn or wart with a surface part of the care product. These devices use one or a combination of attributes to help alleviate pain and aid in healing. They may use a slippery stuff, or a cushion with padding to absorb shock, or a gel filled ampule that acts as a shock absorber or combinations of some of all of these and other properties as well.

U.S. Pat. No. 2,098,312 A (1937) to SCHOLL discloses a common known type of foot pad. It incorporates various thicknesses and or layers of cushioning materials. Some designs may incorporate an area of relief for the addition of additional cushioning material or medicine. In every instance of the pad contacts the area of irritation or sore. There is no aspect that isolates the sore or impediment from being contacted by material from the device. As the person walks the pad will and must contact the sore or callus although cushioned.

U.S. Pat. No. 1,656,135A (1928) to BLANCHFIELD discloses a device namely designed for bunions or corns on the big toe. It incorporates padding to give clearance from the shoe so as to help lessen the sore from pressure or abrasion. It also may incorporate a logically placed hole being cut in the device to lessen pressure on the sore.

U.S. Pat. No. 2,918,056A (1959) LEVITT discloses a foot corrective pad that incorporated various shaped pads made of a cushioning material that may utilize strategically located holes in the devices to help alleviate pressure from various types of foot sores. Yet again there is no mechanical aspect in this device to isolate completely the sore from being touched or pressure being applied to the sore. When the person walks even though the cushion may lessen some pressure it is inevitable that the sore will come in contact with pressure from locomotion from a sock, or shoe sole or shoe lining as the is a hole and not a shield surrounding the sore.

U.S. Pat. No. 8,230,620 B2 (2012) EBEL discloses a foot pad that is much like the common U pad that most everyone is aware of. In this case it is designed specifically for the shape of the heal and not generically shaped for use in various areas on the bottom or other areas of the foot. In the same manner as other disclosed previous art the device does not isolate a pressure point or sore from pressure. It merely attempts to alleviate or put space between the painful area or sore so as to reduce pressure but does not specifically isolate the sore or area from being contacted by some pressure or contact from a sock or shoe or walking surface during locomotion.

U.S. Pat. No. 6,471,986 B1 (2002) CLINE, LUNDY, FERET discloses a corn, callus and wart removing pad. It is a device that has a recessed area for medication of some type that is retained in a strategically located relief area of the pad covered by a tab that is removed before application to the sore. The medicated area is placed over the actual sore. The claims include an improved aspect of retention of the medication to the infected area, a thinner aspect of the pad so as to help minimize pressure to the sore, and an advanced method of retaining adhesion to the skin so the pad stays in place. Again this device does not isolate the sore completely from pressure or abrasion. It merely seeks to provide a lower profile for less contact and a method of more accurate medicine application and better adhesion.

U.S. Pat. No. 1,847,973 A "MORTON" discloses a "Morton Extension" that seeks to extend pressure forward or aft of namely the M1, M2 and/or the M3 metatarsal bone to move walking pressure to either direction to help alleviate pain and or internal sores. It does not incorporate a focusing aspect such as a hard shell cone or device built into the extension that transmits pressure from an isolated pressure point location but rather a general incorporated area.

U.S. Pat. No. 852,023 A (1907) KLOKKE discloses a device that only allows for a retainer of medicine, or cotton padding combined with medicines to help heal the corn. It does not isolate the sore or pressure point from any and all possible pressure or contact from the device itself or a sock or shoe during locomotion.

These prior art examples of callus, wart and foot sore devices are not designed to completely isolate the specific sore or area of irritation from "all" pressure or abrasion. They are not designed to transfer all pressure or abrasion to an area separate from the intended sore or pressure point. Specifically "U Pads" attempt to lessen pressure and exacerbation by providing a super thick spacing function between the sore and the shoe bed so as to lessen pressure. The amount of cushioning required to completely isolate the sore from pressure is not comfortably possible in most circumstances. These afore mentioned devices do not isolate the sore completely from being touched by part of the device, bandage, padding, sock or surrounding materials in the shoe itself. Over the counter shoe inserts and generic orthotics are available for various foot sores and conditions. Podiatrists can offer custom made orthotics that typically are used for correcting improper alignment of the foot so as to retard or help alleviate pressure related sores or muscular damage or conditions of the foot. In the foot bed of an orthotic device is often used an area of relief with indentation or a heavily padded area directly adjacent to the sore designed to help lessen the amount of pressure on the actual sore. Something comparable to a "mortons extension" with numerous different configurations may be built into the orthotic. These pressure re-direction apparatuses are designed to change the way the foot articulates so as to assist in therapy of the numerous unhealthy sores and conditions possible caused by improper foot mechanics under locomotion.

SUMMARY OF THE INVENTION

The present invention in its simplest form is designed to isolate and redirect pressure that is normally associated with the cause of Intractable Plantar Keratosis or "IPK". Unlike aforementioned prior art examples discussed, the present invention incorporates a specifically designed incompressible indentation in a plastic disc or made of other suitable material. The material may use generic or strategically placed venting holes or be made of a porous material to supply a breathable function aspect so as to allow air if desired to interact with the sore. In the simplest form the indentation is designed with a conical aspect. The device is applied to the bottom of the foot with the point or narrowest aspect of the cone facing away from and directly over and in line with the exact physical irritation point that in most cases is the causal link in the promotion and growth of the associated "IPK" sore or callus.

The round disc is especially thin and stiff so as pressure is applied to the disc the conically shaped aspect with its indentation and dedicated point will maintain rigidity and transfer the pressure around the sore. The area under the conical aspect of the disc is relieved adequately. The disc is stiff enough mechanically so that no part, or an insignificant part, of the conical weight transferring point and relief area comes in contact with the callus. Pressure from walking or locomotion is transferred through the conical point and sides of the conical extrusion to the area surrounding the sore. This keeps practically all the pressure off of the irritation point thereby alleviating and or minimizing the force associated with the causal action of the condition known as "IPK". Shifting the pressure away from the irritation point by means of the weight transferring feature of the present invention provides that the irritation point is no longer exacerbated. The application of a correctly fitted remotion disc over the "IPK" callus and irritation point provides immediate cessation of pain caused from pressure to the callus or sore.

Typical debriding of the callus or sore aids in maintaining clearance between the conical recess of the disc and the IPK callus. The healthy flesh around the callus can then bear the load from the load distributing flat surface aspect of the disc.

The new and present invention remotion disc implements a mechanical disbursement advantage that displaces pressure away from a callus or sore.

Typically the base of the disc is flat and round but is not limited to any particular shape as the base aspect can be made to function in areas of the foot or body where a different shape may be more suitable for the application. The base aspect could be flat or curved or in a customizable version made to fit the contour of the application location.

For other conditions besides "IPK" the discs can be made with larger conical cones, broader and flatter cones, elongated cones, triangular prism, cubic, pyramid, cuboid, dome, elongated dome or custom shapes for various sizes and shapes and types of sores. In all of these different applications the feature of the remotion disc having an exceedingly strong and incompressible weight transferring cupola of some type is key. The larger the weight transferring shape is needed the stiffer the disc and associated cupola will necessarily be so as to remain immovable and uncompressible under locomotive pressure. The depth of the protective shape or point must be enough so that when the disc is put under pressure the weight is transferred effectively to the surrounding base or weight disbursement aspect of the disc and thereby to the surrounding flesh effectively keeping any part of the protective cupola or dome from significantly contacting or significantly applying pressure to the sore or irritation point.

When the remotion disc is in place there is no need for thick padding between the sore and the shoe or walking surface. The ultra-thin aspect of the new invention typically cannot even be noticed during locomotion or at rest.

The present invention may or may not lead to an actual cure of the callus or condition. The device effectively isolates the irritation point so that the body does not attempt to produce or continue to create a callus or sore to protect the irritation point from pressure. When the pressure is removed the irritation point is allowed to heal itself. In some cases complete cessation of the IPK sore may occur. However, it depends on the initial cause of the IPK or irritation point. An IPK condition can be brought on by a period of repetitive movement for a period of time that a person would not normally be inclined to do. For example a person decides to do a job requiring a very repetitive leaning back and forth on one foot for an unusual amount of time. A person that has never subjected the foot to such focused and repetitive pressure on a particular metatarsal structure may exacerbate an irritation point. This inflammation can trigger the body to form a callus to protect that inflamed irritation point thereby causing a reaction or condition known as "IPK". The new and present invention may in fact be able to completely reverse this condition as the IPK had been propagated by excessive and abnormal repetitive pressure to the metatarsal bones. Being that this odd occurrence may never happen again, isolating the IPK sore with the present invention can completely reverse the condition. If the person never partakes of the same repetitive abuse to the foot again, the condition can disappear completely with use of the present invention.

If the IPK is due to abnormal foot mechanics, bone spurs, accidental damage to the foot or accumulative damage to the metatarsal bones over time under typical and natural locomotive pressure of the individual, then the present invention may only aid in pain management. However, it is possible that the present invention could aid in healing the condition used in conjunction with medically sound therapies and or surgical operations with or without the use of custom orthotics. The orthotics could certainly utilize the present invention's weight transferring mechanical design aspect to aid in removing pain and/or aiding in therapy of the condition. The present invention may be able to be used in these other cases of IPK to manage pain and/or growth of the callus, thereby negating the need for immediate surgery. It is possible that in some cases therapeutic use of the present invention could negate the need for surgery altogether. It may also save the patient the cost of expensive custom made orthotics. Patients that utilize the present invention should use the remotion disc with the guidance of a podiatrist to assure best results.

The mechanical aspect of the present invention can also be implemented in therapy in the treatment of another very common and often deadly and seriously debilitating medical condition known as bed sores. Bed sores are typically understood to be caused from prolonged pressure and or irritation to the flesh in numerous areas of the human body. The present invention would be using remotion discs designed in different shapes and sizes and various contours with logically shaped cupolas to fit various areas of the human body. The weight transferring aspect using a dome or cone or custom cupola shape of myriad designs as mentioned afore could also be used to treat bed sores. The present invention could also be made to help treat cuts, calluses, burns, sores, etc. with the considerations in design depending on the height and width and location of the sore on the body. There can also be a customizable form of the present invention. Positive molds of the body and sore location would be produced with any of the various molding materials available. Once the positive model of the body contour area and shape of the sore are completed, the mold would be placed in a vacuum forming machine. Sterile or food grade plastics of various types and thickness can be vacuum formed to the body mold, and a remotion disc would be formed. To allow clearance between the cupola aspect of the remotion disc a determined amount of spacer material such as gauze would be put in-between the vacuum form body mold and the plastic sheet to be vacuum formed. The vacuum forming process would be actuated thereby leaving a clearance space between the sore and the cupola of the remotion disc.

After the remotion disc is vacuum formed the spacer material is removed from the cupola area of the remotion disc, thereby allowing space between the "sore" and the cupola which is the pressure transferring aspect of the remotion disc. It would then provide the same mechanical advantage of displacing pressure and abrasion away from the sore to surrounding areas of healthy flesh, thereby removing acerbation and abrasion and pain caused by pressure and abrasion as in all previous examples of remotion discs.

There are myriad types of adhesives and tapes that could be incorporated into the new and present invention. It could be held in place with a simple peel and stick adhesive or some type of bandaging or surgical tape. When using the simplest form of the new present invention for an "IPK" callus or sore, it is critical that the remotion disc is held in place with the cone or cupola or remotion indentation aspect directly over the irritation point. In numerous tests the use of a typical plastic surgical tape helped affix the remotion disc in proper location better than a typical peel and stick adhesive. The use of a good quality surgical tape covered the disc entirely and the skin area immediately around the remotion disc. This tended to keep the remotion disc most precisely in place as the overlap of the tape over the edge of the disc created a sort of envelope for the disc to sit in. When locomotion attempts to push the remotion disc in one direction or the other the edge of the disc is pushed up against the tape that is overlapping the disc and stuck down and around the edge of the disc to the skin. A typical peel and stick adhesive on the disc part only would not create the associated edge of a pocket or the envelope created when using tape. A standalone adhesive on the disc may allow the remotion disc to be pushed one way or the other under causing the disc to move out of position during locomotion.

These and other features and advantages of the Pressure Remotion Disc reside in the construction of parts and the combination thereof, the mode of operation and use, as will become more apparent from the following description, reference being made to the accompanying drawings that form a part of this specification wherein like reference characters designate corresponding parts in the several views. The embodiments and features thereof are described and illustrated in conjunction with systems, tools and methods which are meant to exemplify and to illustrate, not being limiting in scope.

BRIEF DESCRIPTION OF THE DRAWINGS

Having thus described the various embodiments of the invention in general terms, reference will now be directed to the included drawings, which may or may not be drawn to scale and wherein:

FIG. 1 is top plan view of embodiment 100 that illustrated a remotion disc that may likely include the most common design considerations of the various embodiments.

Figure 16:
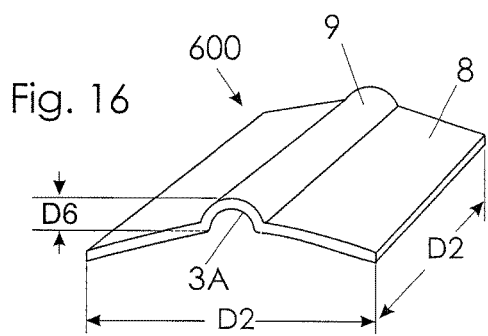
Figure 17:
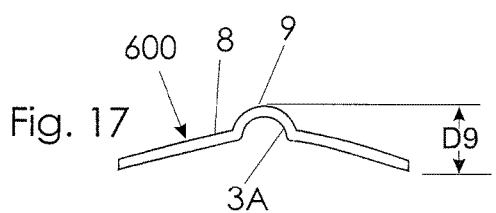
Figure 18:
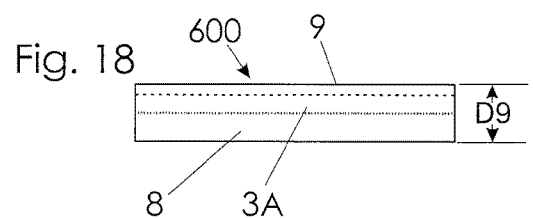
Figure 19:
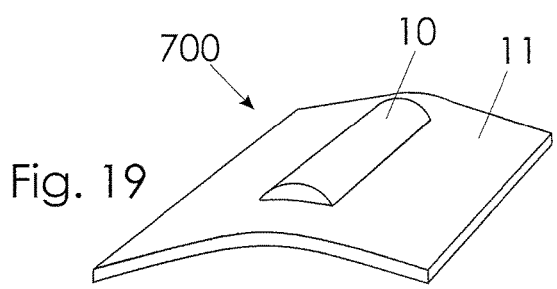
Figure 20:
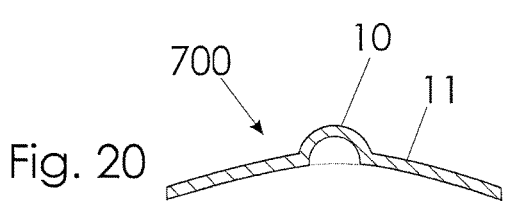
Figure 21:
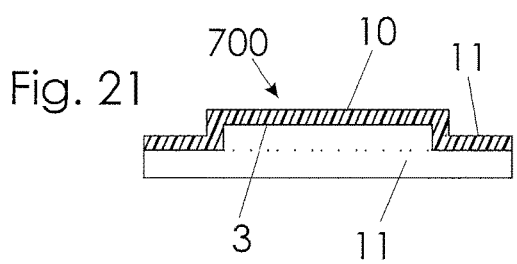
Figure 22:
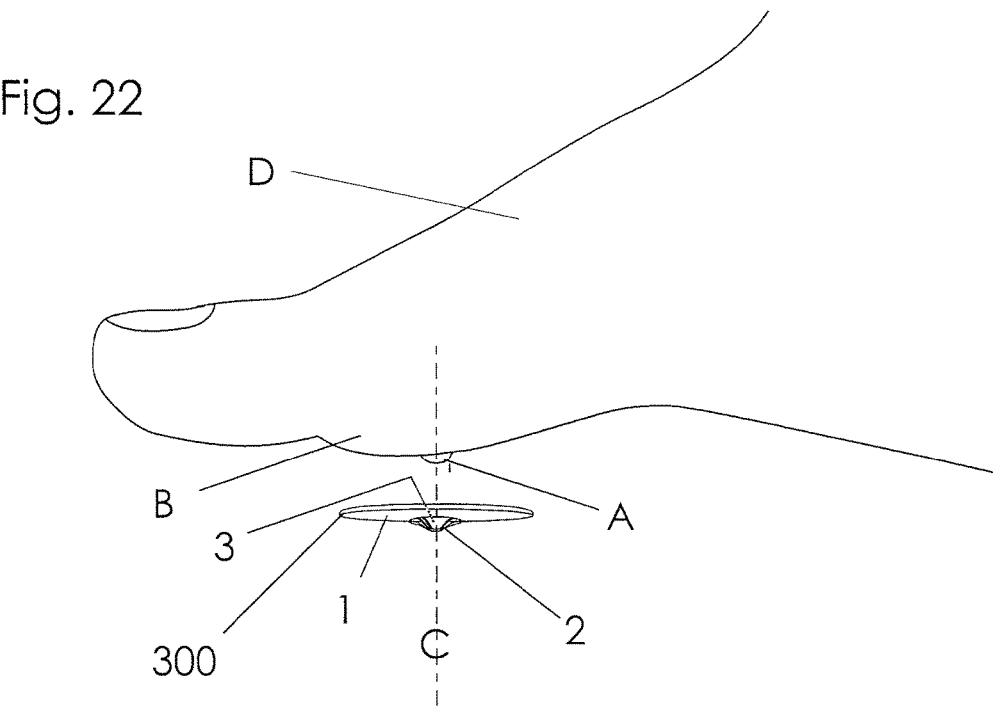
Figure 23:
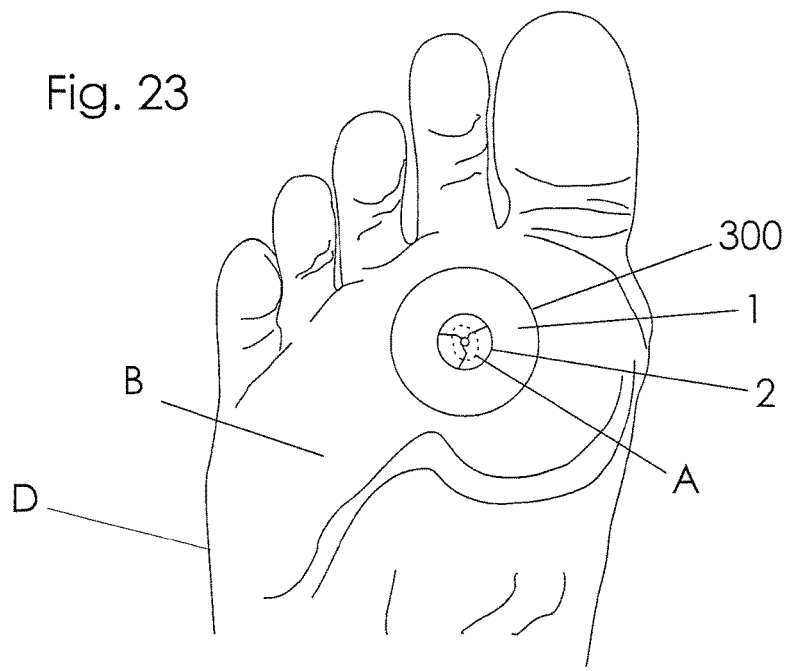
Figure 24:
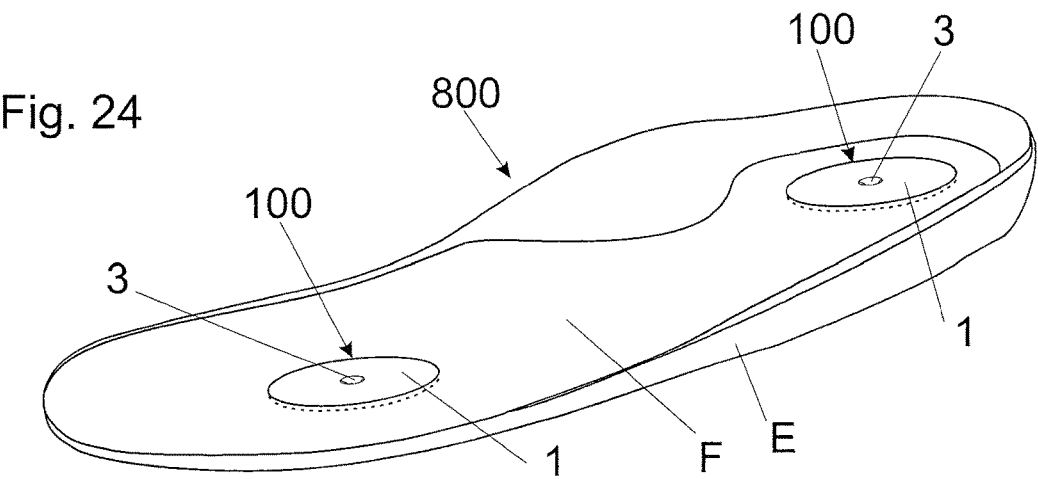
Figure 25:
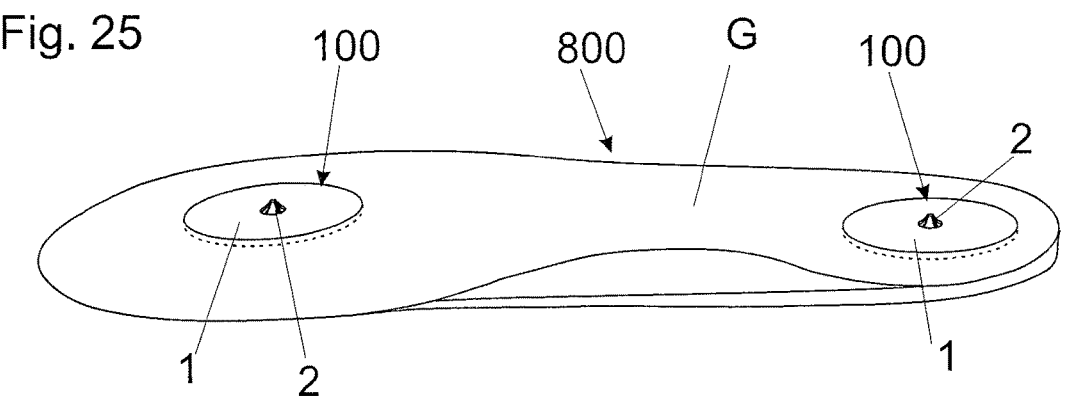
Figure 26:
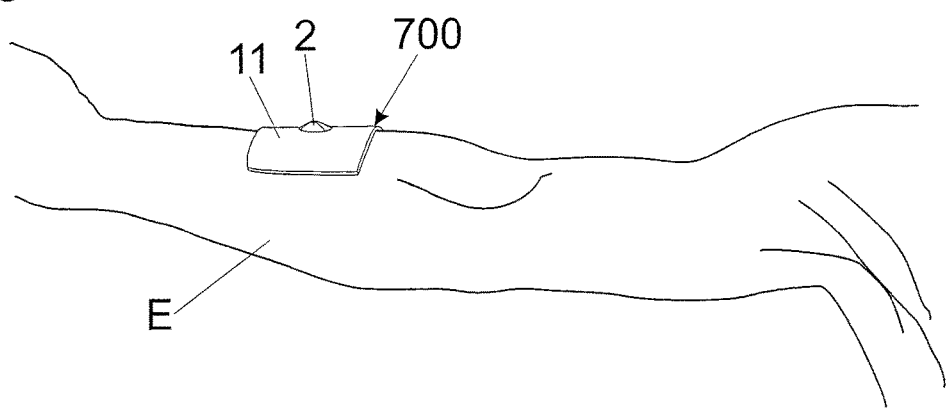

FIG. 2 is a bottom perspective view of embodiment 100.
FIG. 3 is a top perspective view of embodiment 100.
FIG. 4 is a cross sectional view of embodiment 100.
FIG. 5 is a top plan view of embodiment 200.
FIG. 6 is a bottom perspective view of embodiment 200.
FIG. 7 is a top perspective view of embodiment 200.
FIG. 8 is a cross sectional view of embodiment 200.
FIG. 9 is a bottom perspective view of embodiment 300.
FIG. 10 is a cross sectional view of embodiment 300.
FIG. 11 is a top plan view of embodiment 300.
FIG. 12 is a top plan view of embodiment 400.
FIG. 13 is a cross sectional view of embodiment 400.
FIG. 14 is a top plan view of embodiment 500.
FIG. 15 is a cross sectional view of embodiment 500.
FIG. 16 is a bottom perspective view of embodiment 600.
FIG. 17 is a side elevation view of embodiment 600.
FIG. 18 is a longitudinal cross sectional view of embodiment 600.
FIG. 19 is a bottom perspective view of embodiment 700.
FIG. 20 is a cross sectional view of embodiment 700.
FIG. 21 is a longitudinal cutaway view of embodiment 700.
FIG. 22 is a side elevation view of embodiment 300 as applied to a foot.
FIG. 23 is a bottom plan view of embodiment 300 applied to foot.
FIG. 24 is top perspective view of embodiment 800.
FIG. 25 is a bottom perspective view of embodiment 800.
FIG. 26 is a top perspective view of embodiment 700 on a human arm.

Before explaining the disclosed embodiments in detail, it is to be understood that the embodiments are not limited in application to the details of the particular arrangements shown, since other embodiments are possible. Also, the terminology used herein is for the purpose of description and not of limitation.

DETAILED DESCRIPTION OF THE DRAWINGS

Various embodiments of the invention are described more fully hereinafter with reference to the accompanying drawings, in which some, but not all the embodiments of the invention are shown in the figures. Indeed, these inventions may be embodied in many different forms and should not be construed as limited to the embodiment set forth herein: rather, these embodiments are provided so that this disclosure will satisfy applicable legal requirements.

FIG. 1 illustrates embodiment 100 of the invention. In the simplest form the embodiment 100 is applied to the plantar aspect of the human foot. Embodiment 100 is the simplest form of a remotion disc that is designed principally for the treatment a medical condition known as Intractable Plantar Keratosis or "IPK" for short, typically found on the ball of the foot. As shown in FIG. 1 there is a round disc 1 with a conical dome 2 located in the center of 1. The top is labeled T. The disc 2 describes from the top T. On a bottom of the foot callus, the disc 2 descends away from the callus. See FIG. 22. The center of the disc is labeled 20. FIG. 2 shows a perspective view of the bottom of embodiment 100 that reveals an exceeding thin disc 1 (about 0.04 inch) with a conical dome or extrusion 2 that is approximately the same height as disc 1 is thick (about d4=0.04"). The low profile of disc 2 is exceeding rigid and provides an incompressible recess 3 of FIG. 3 which is installed and positioned directly over the callus, sore or irritation point and/or the IPK causal point. The rigid disc 1 is installed to the bottom of the foot being held in place by an appropriate adhesive tape (not shown). The cone 2 is inversely situated directly above and directly in line with the callus center or the causal center point of irritation. The recess 3 surrounds the callus and/or the irritation point but does not impinge upon it. As pressure is put upon embodiment either by standing or locomotion, disc 1 working in concurrence with the rigid disc 2 and recess 3 redirects the pressure. The pressure is redirected and transferred to the area around the callus or causal irritation point, thereby mitigating pain and acerbation that typically and most often painfully and obstinately persists. Transferring weight and pressure down the sides of cone 2 on to disc 1 isolates the callus or causal irritation by means of recess 3 and remarkably reduces pain as well as abating further acerbation.

FIG. 2 shows the bottom view of embodiment 100 with the conical extrusion 2 shown protruding below the disc 1. The tip 20 of disc 2 comes in contact with the walking surface before disc 1 contacts the walking surface thereby, due to is rigidity, transferring pressure down the sides of the cone 2 to disc 1.

FIG. 3 shows the top side of embodiment 100 which reveals the recess or cavity 3 that is a common feature among all of the various embodiments. Recess 3 can be various sizes and shapes depending on the particular callus, blister or sore that is being isolated.

FIG. 4 exposes the recess cavity 3 and the height of disc 2 in relation to disc 1. The height and width and thickness of cone 2 and disc 1 determine the height of recess 3. Nominal dimensions are d1=0.125", d2=1.0", d3=0.09 to 0.10", d4=0.04", d5=0.0625".

FIG. 5 shows embodiment 200 showing the feature of air holes 5 typically located on disc 1 to allow callus or sore and the flesh around the sore to breathe. Hole diameter d5 is about 0.0625". This feature can be approached in different methods such as more holes 5 in different areas, less holes, larger holes, or holes in cone 2. The breathability may also be achieved by using a porous substrate to produce the same effect as holes 5 in embodiment 200.

FIG. 6 shows embodiment 200 with cone 2 and disc 4 with no need to expound on it being mechanically similar to embodiment 100 except for the air breathing holes 5 and their capability.

FIG. 7 shows the top side T of disc 200 with similar construction and function of disc 100 except for the air breathing feature of typical holes 5.

FIG. 8 needs shows the cutaway of embodiment 200 and discloses the air holes 5.

FIG. 9 discloses embodiment 300 with the only difference between embodiment 100 is the addition of an adhesive 6 shown in FIG. 11 as adhesive 6 so as to be applied to the body without the use of tape. FIG. 10 shows the adhesive layer 6 and a removable backing 60.

FIGS. 12 and 13 disclose embodiment 400. For all intents and purposes its function is intrinsically the same as all of the other embodiments. However, the dome 7 is shown larger and to be dome shaped instead of conical like 2 disc. Recess 3 is larger and will accommodate a larger excrescence, d6=0.125", d7=0.1875", FIGS. 14 and 15 disclose embodiment 500, wherein d8=0.5". For all intents and purposes function is intrinsically the same as all of the other embodiments. However, the dome 8 is shown oblong and flattened instead of conical and like conical disc 2 or domed disc 7. Recess 3 is larger and dependent on the shape and size of 8 and thus will accommodate a larger and different shape excrescence.

FIGS. 16 and 17 and 18 disclose embodiment 600, with D9=0.20 inch. Elongate dome 9 extends the entire disc 8. For all intents and purposes its function is intrinsically the same as all of the other embodiments. However, the cupola 9 is shown as dome shaped and runs the entire length of disc 8 which compared to other embodiments serves the same function as disc 1 & 4. This design allows a protective weight transfer function for a sore that is longer than it is wide. It is also shaped to fit the contour of a body part. This aspect is part of the customizable version of the remotion discs in general. In a scenario dealing with embodiment 600 a laceration on the hind quarter of the buttocks may benefit from the transference of pressure via the long cupola 9 allowing a person to sit directly on the remotion disc 600 thereby transferring weight and possible damage away from the laceration allowing it to heal and scab over without being acerbated or damaged during the healing process. The embodiment 600 would allow the patient to sit with the laceration in isolation, thereby removing pain from the pressure as well. The laceration would also receive healing benefits from air breathing benefits from recess 3A which allows air to the wound as recommended.

FIGS. 19, 20 and 21 disclose embodiment 700 which like the preceding embodiments do not need detailed discussion. The difference of embodiment 700 is cupola 10 which is hollow like dome 9 in embodiment 600 but is not open ended. The form fit to a contour of the body is noted as disc 11.

FIG. 22 is a side view of a foot D and embodiment 300 being located in proper position before installation over an "IPK Sore A". B is the Ball of the human foot. Recess 3 is placed directly in line with the center C of the IPK SORE A and over top of A with cone 2 situated away from A and B on the foot D.

FIG. 23 discloses a bottom view of the foot D and an IPK Sore A on the ball of the foot B with the proper alignment and installation of embodiment 300. Sore A is directly under the center point of 2. Recess 3 is covering the sore A. Disc 1 is applied to and affixed to the flesh around sore A on ball B by means of adhesive feature 6 shown in FIG. 11.

FIG. 24 discloses the top perspective view of embodiment 800 which is an orthopedic shoe insert. Embodiment 100 is shown embedded flush with the foot bed F of the orthopedic insert E in two different locations. One is located under the ball of the foot and the other in the heel. The orthotic may or may not have two embodiments 100 installed in the orthotic. It may have combinations of different embodiments fabricated in the orthotic depending on the needs of the wearer. Only recess 3 can be seen from the top in FIG. 24 because feature 2 is purposely installed away from the foot D as shown in FIG. 25.

FIG. 25 is a bottom view of embodiment 800. The disc of embodiment 100 is installed flush with the bottom G of the orthotic E. Cupola 2 protrudes from disc 1 and because disc 1 is flush with G the cupola 2 contacts the shoe and walking surface first. The only difference in the case of embodiment 800 versus the other various embodiments is that constructs of various embodiments are installed in permanent location in the foot bed F of an orthotic E as needed. Because of this aspect the remotion disc will be held in proper location to the sore via placement and being affixed in the orthotic insert 800.

A value of 25% plus or minus of these specs necessary to cause the force lines to follow from the tip of the cone down the cone sides and into the base of the disc so that the force lines continue out to the edge of the disc.

The aperture point or where the cone connects to the disc must be rigid enough so as to make sure the flat disc part of approximately 1" in diameter for the main embodiment does not flex below the plane of the disc itself thereby allowing the pressure to radiate from the center out in all directions to the outside edge of the disc, thereby spreading the pressure out and away from the callus cells or sore area underneath the point/cone and the aperture connection point.

The thickness of a typical remotion disk for IPK would be from 0.030 inches to 0.045 inches in thickness. Younger and lighter children could get by with a plastic remotion disc with the same specs as above but could be a 0.030 thickness disc. An adult male of nearly any weight up to 400 lbs will be able to use a remotion disc of 0.040 thickness with the same specs.

Of course if for custom applications where the span may be larger than the typical remotion disc the plastic of same spec but thicker can be used. The range is determined by the size of area to be isolated from pressure. The remotion discs could be made as thick as 0.080 to 0.100 in some instances if needed. The specifications for the plastic above is sufficient to work in most any application with a proper thickness being utilized.

Like fenders on a car there can also be incorporated details such as folds, ribs or creases, embossing and various types of indentations to help shore up rigidity if covering a larger span is necessary for in the case of a custom use for bedsores.

Device methodology concerning IPK: The cupola or shroud does not have to be larger than the outer area of the callus itself because most importantly is that the causal point or irritation point is isolated. So part of the bottom of the disc can actually rest on the flattened or sanded flat callus tissue, as the disc is stiff enough to carry the force lines over top of and spread it to enough of the surrounding area so that the callus core does not impinge on the irritation point causing acerbation.

The discs can have the following physical properties. Plastic having these properties are preferred.

| Property | Test Method | Units | Values |
|---|---|---|---|
| PHYSICAL | | | |
| Specific Gravity | ASTM D 792 | — | 12 |
| Refractive Index | ASTM D 542 | — | 1.586 |
| Light Transmission, Clear @ 0.118" | ASTM D 1003 | % | 86 |
| Light Transmission, I30 Gray @ 0.118" | ASTM D 1003 | % | 50 |
| Light Transmission, K09 Bronze @ 0.118" | ASTM D 1003 | % | 50 |
| Light Transmission, I35 Dark Gray @ 0.118" | ASTM D 1003 | % | 18 |
| Water Absorption, 24 hours | ASTM D 570 | % | 0.15 |
| Poisson's Ratio | ASTM E 132 | — | 0.38 |
| MECHANICAL** | | | |
| Tensile Strength, Ultimate | ASTM D 638 | psi | 9,500 |
| Tensile Strength, Yield | ASTM D 638 | psi | 9,000 |
| Tensile Modulus | ASTM D 638 | psi | 340,000 |
| Elongation | ASTM D 638 | % | 110 |
| Flexural Strength | ASTM D 790 | psi | 13,500 |
| Flexural Modulus | ASTM D 790 | psi | 345,000 |
| Compressive Strength | ASTM D 695 | psi | 12,500 |
| Compressive Modulus | ASTM D 695 | psi | 345,000 |
| Izod Impact Strength, Notched @ 0.125" | ASTM D 256 | ft · lbs/in | 18 |
| Izod Impact Strength, Unnotched @ 0.125" | ASTM D 256 | ft · lbs/in | 60 (no failure) |
| Instrumented Impact @ 0.125" | ASTM D 3763 | ft · lbs | >47 |
| Shear Strength, Ultimate | ASTM D 732 | psi | 10,000 |
| Shear Strength, Yield | ASTM D 732 | psi | 6,000 |
| Shear Modulus | ASTM D 732 | psi | 114,000 |
| Rockwell Hardness | ASTM D 785 | — | M70/R118 |
| THERMAL | | | |
| Coefficient of Thermal Expansion | ASTM D 696 | in/in/° F. | $3.75 \times 10^{-5}$ |
| Coefficient of Thermal Conductivity | ASTM C 177 | BTU · in/ hr · ft² · ° F. | 1.35 |
| Heat Deflection Temperature @ 264 psi | ASTM D 648 | ° F. | 270 |
| Heat Deflection Temperature @ 66 psi | ASTM D 648 | ° F. | 280 |
| Brittleness Temperature | ASTM D 746 | ° F. | −200 |
| Shading Coefficient, clear @ 0.236" | NFRC 100-2010 | — | 0.97 |
| Shading Coefficient, Gray or Bronze @ 0.236" | NFRC 100-2010 | — | 0.77 |
| U factor @ 0.236" (summer, winter) | NFRC 100-2010 | BTU/hr · ft² · ° F. | 0.85, 0.92 |
| U factor @ 0.375" (summer, winter) | NFRC 100-2010 | BTU/hr · ft² · ° F. | 0.78, 0.85 |
| ELECTRICAL | | | |
| Dielectric Constant @ 10 Hz | ASTM D 150 | — | 2.96 |
| Dielectric Constant @ 60 Hz | ASTM D 150 | — | 3.17 |
| Volume Resistivity | ASTM D 257 | Ohm · cm | $8.2 \times 10^{16}$ |
| Dissipation Factor @ 60 Hz | ASTM D 150 | — | 0.0009 |
| Arc Resistance | | | |
| Stainless Steel Strip electrode | ASTM D 495 | Seconds | 10 |
| Tungsten Electrodes | ASTM D 495 | Seconds | 120 |
| Dielectric Strength, in air @ 0.125" | ASTM D 149 | V/mil | 380 |
| FLAMMABILITY | | | |
| Horizontal Burn, AEB | ASTM D 635 | in | <1 |
| Ignition Temperature, Self | ASTM D 1929 | ° F. | 1022 |

-continued

| Property | Test Method | Units | Values |
|---|---|---|---|
| Ignition Temperature, Flash | ASTM D 1929 | °F. | 824 |
| Flame Class @ 0.060" | UL 94 | — | HB |
| @ 0.394" | UL 94 | — | V-0 |

I, Barry Mack, the inventor of the Remotion Disc contacted a condition known as Intractable Plantar Keratosis (herein IPK) on the bottom of the foot that develops for various reasons but namely a prominence of bony structure or spur or misalignment of the foot anatomy that perpetuates the inordinate pressure applied to a small and somewhat isolated irritation point. This pressure and irritation basically causes a callus to form as the body is attempting to cushion the irritation point or causal point of the callus.

I visited three different podiatrists over a year period of time. I was told by all of them that I would most likely suffer with it for the rest of my life. They all gave me their treatment recommendations and regimens to consider and or follow.

All of them recommended the commonly known U-Pads which are found at every foot care section of any reputable drug store or pharmacy over the counter. They are generally horseshoe shaped and are about 0.1875" thick and are made of a semi firm foam rubber. They are positioned so that the callus and irritation point is located in the void of the pad where the interior aspect of the pad is radiused. The method is to allow the area of the foot to absorb some of the pressure onto the rubber pad thereby lessoning the actual pressure absorbed by the callus or irritation point. This pad is usually applied after debriding or sanding down the callus.

I was told by all three podiatrists that this method will only help alleviate some of the pain and hopefully slow down the return growth of the callus. With this treatment I would have to return to the Podiatrist approximately every 3 weeks for maintenance debriding and to continue wearing the U-Pads.

Another recommendation was using a round disc type pad much like the U-Pad but it was round with a hole or aperture rather than the slot in the U-Pad. I was given the same instructions with the same results.

All three Podiatrists recommended expensive generic and/or custom made orthotics so as to cause my foot to work in proper alignment under locomotion. The very expensive generic orthotics recommended resulted in miserable results. The IPK continued to grow and be very painful with the addition of new calluses growing on my foot in other new locations.

All three podiatrists said I could attempt a surgical procedure but was warned that it may only cause the IPK to move to a new location. They all recommended that I try an extended program of using the U-Pads or Round donut pads and do surgery as a last resort. They did note that it may be a lifelong management routine but would be better than surgical complications.

I opted for the pad treatment and debriding program. It became so painful and problematic that I had to give up tennis and could not run of jog anymore and always had a limp caused from the pain continually. I was so desperate I attempted to embed the U-Pads into a shoe insole in an attempt to help. It did not help the condition whatsoever. As months went by I had come to believe that without a miracle or attempting surgery I would be limping around like a lame animal for the rest of my life.

Being an inventor I was reminded of the statement that all three Podiatrists said numerous times, "The irritation point causes the growth of the callus." I kept thinking "point", the irritation point. I thought to myself and questioned could it be as simple as removing the pressure completely from that irritation point? I reasoned that the U-Pads or donut pads would never isolate that point completely as the flesh would collapse through the slot or aperture. The irritation point would necessarily have some type of pressure applied to it with these devices. I realized that the present invention device would have to assure that none or a very minute amount of pressure could touch that irritation point.

I conceived a thin non-flexible disc with a hollow come in the center of it that was exceedingly stiff so that when it was placed down and away from and in line with the exact center of the irritation point, the point an disc would not collapse under the weight of locomotion. This would cause the pressure to be pushed away from the very small but super sensitive irritation point.

I continued to turn it into reality. I grabbed a 1 mm thick guitar pick made out of plastic and cut it in the shape of a circle. I heated a 16 penny nail with my propane torch and used it to push an indent into the disc. It looked nearly exactly as the embodiment 100.

I debrided the callus flat and then I taped it to the bottom of my foot with the cone or point down with no other U-Pad or device. The very first step was a miracle. I could not feel the sharp pain go up into my foot. I could not believe it. I walked for the first time in over 15 months as though I did not have the IPK. I was in so much joy I hopped up and down like a kid repeatedly without any debilitating pain.

My son and I played tennis for over an hour that very moment. After returning from playing I took the disc off to see if I was just imagining things. The moment I removed it and tried to walk I was limping again in agony. It really did work.

So then I immediately put the Remotion Disc back on. I continued to wear the disc night and day for the next few weeks. I noticed after that time I did not have to debride the callus. It had not grown back. I canceled my next appointment with my Podiatrist. I kept wearing the device and slowly but surely the callus started to disappear. I noticed the pain was getting less and less. After 3 months of wearing it I decided to walk without it on to see if any pain or that burning sensation was present. I could feel a slight burning sensation directly on the center irritation pint of the IPK, so I decide to wear the Remotion Disc for another month. So a month later I removed it again and felt no pain or burning sensation at all. But being I did not want it to ever come back I decide to wear it for another month to make sure. A month later I removed the Remotion Disc and years later have never had to use it again. My IPK is completely healed and has never returned. The same IPK that three licensed Podiatrists told me I would have for the rest of my life.

The consensus among my Podiatrists is that the exceedingly stiff disc with the rigid cone causes force lines to be moved away from the irritation point of the callus, and thus removes acerbation which causes callus cells to grow.

These drawings do not limit the use of the various embodiments within the numerous shapes or sizes and materials whether full or partial in length or custom shaped designed orthotic inserts that one skilled in the art would readily comprehend.

While a number of exemplifying features and embodiments have been discussed above, those of skill in the art will recognize certain modifications, permutations, additions and subcombinations thereof. No limitation with respect to the specific embodiments disclosed herein is intended or should be inferred.

I claim:

1. A disc for application to a human body, said disc comprising:
    a hard round disc having a center point;
    said disc having a top surface with an adhesive capable of adhering said disc to a bottom of a foot over a callus;
    a bottom surface of said disc having a hollow concave dome relative to the top surface;
    said hollow concave dome having a center point in alignment with the center point of the disc;
    a diameter of the hollow concave dome slightly larger than a diameter of an irritation area of the callus;
    a hardness of the disc ranging from about 25% plus or minus Rockwell Hardness M70/R118;
    a thickness of the disc ranging from about 0.03" to about 0.04" inches so as to remain stiff and not bend as a weight of the foot and a human is applied downward on the disc;
    said disc having a diameter ranging from about 25% plus or minus Rockwell Hardness M70/R118; and
    said hollow concave dome having a recess about one thousandths inch to about five thousandths inch deeper than a height of the callus.

2. The disc of claim 1, wherein the hollow concave dome is elongate and semi-cylindrical.

3. The disc of claim 2, wherein the hollow, concave elongate dome extends fully across the disc.

4. The disc of claim 2, wherein the hollow, concave elongate dome extends partially across the disc.

5. The disc of claim 1 further comprising air holes.

6. The disc of claim 1, wherein the hollow concave dome is round.

7. A disc for application to a human body for displacing pressure and relieving pain, the disc comprising:
    a generally square shape having a center point;
    an arched body forming a concave central top area for application to a callus on a human;
    an elongate dome extending through the center point and at least partially across a longitudinal axis of the disc;
    said disc having a hardness ranging from about 25% plus or minus Rockwell Hardness M70/R118;
    said disc having a thickness from about 0.03" inch to about 0.04" inch;
    said elongate dome having a width and a length slightly larger than an irritation area of the callus; and
    an attachment means functioning to adhere the round disc onto the human body over the callus aligned with the center point of the disc.

8. The disc of claim 7, wherein the attachment means further comprises as adhesive.

9. The disc of claim 8, wherein the adhesive means is attached to the concave central top area.

10. The disc of claim 8, wherein the adhesive means further comprises a tape attached over at least a portion of the bottom of the disc.

11. The disc of claim 8, wherein the adhesive means further comprises an orthotic substrate that supports the dome over the callus.

12. A disc for application to a human body for displacing pressure and relieving pain, the disc comprising:
    a substantially round disc having a center point;
    said round disc having a diameter ranging from about one half inch to about one and a half inches;
    said round disc having a hardness ranging from about 25% plus or minus Rockwell Hardness M70/R118;
    said round disc having a thickness ranging from about 0.03" to about 0.04" inch;
    said round disc having a smooth top surface suited for application to a human body with a callus;
    a hollow dome depending down from a bottom surface at the center point;
    said hollow dome sized to a diameter slightly larger than the callus; and
    an attachment means functioning to adhere the round disc onto the human body over the callus with a center of the callus aligned with the center of the round disc.

13. The disc of claim 12, wherein the attachment means further comprises an orthotic substrate that supports the disc in a co-axial alignment with a center of the callus.

* * * * *